United States Patent [19]
Holcomb

[11] Patent Number: 4,888,113
[45] Date of Patent: Dec. 19, 1989

[54] MAGNETIC WATER TREATMENT DEVICE

[76] Inventor: Robert R. Holcomb, P.O. Box 779, Hamilton, Ala. 35570

[21] Appl. No.: 291,354

[22] Filed: Dec. 29, 1988

Related U.S. Application Data

[63] Continuation-in-part of Ser. No. 934,568, Nov. 21, 1986, abandoned.

[51] Int. Cl.$^4$ .............................................. C02F 1/48
[52] U.S. Cl. ............................ 210/222; 55/100; 210/695
[58] Field of Search ............... 210/222, 223, 232, 695; 123/536, 538; 55/2, 3, 100; 184/6.25

[56] References Cited

U.S. PATENT DOCUMENTS

| | | | |
|---|---|---|---|
| 3,228,878 | 1/1966 | Moody | 210/222 X |
| 4,210,535 | 7/1980 | Risk | 210/222 |
| 4,265,754 | 5/1981 | Menold | 210/222 |
| 4,265,755 | 5/1981 | Zimmerman | 210/222 |
| 4,293,410 | 10/1981 | Strenli et al. | 210/222 X |
| 4,367,143 | 1/1983 | Carpenter | 210/222 |
| 4,519,919 | 5/1985 | Whyte et al. | 210/695 |
| 4,572,145 | 2/1986 | Mitchell et al. | 210/222 X |
| 4,605,498 | 8/1986 | Kulish | 210/695 X |

FOREIGN PATENT DOCUMENTS

| | | | |
|---|---|---|---|
| 1155086 | 10/1983 | Canada | 210/222 |
| 8503649 | 8/1985 | PCT Int'l Appl. | 210/222 |

OTHER PUBLICATIONS

Aqua-Flow TM spec sheet and information (4 pages), 1983.
Advanced Research Projects Agency, Magnetic Treatment of Water, 1973.
Szostak & Toy, Magnetic Fluid Conditioning System Allows 3,000 ppm Hardness Without Cooling Tower Scale Buildup, Chemical Processing, 1985, 44–45.
Grutsch & McClintock, Corrosion and Deposit Control in Alkaline Cooling Water Using Magnetic Water Treatment at Amoco's Largest Refinery, International Corrosion Forum, paper No. 330, 1984.
Permag Magnet Catalogue, No. P5A, p. 10, 1986.
Walker, The Amateur Scientist, Scientific American, pp. 134–138 (Feb. 1987).

*Primary Examiner*—W. Gary Jones

[57] ABSTRACT

A magnetic water treatment device for the treatment of water in a non-ferrous pipe is provided. The device is constructed of an elongated aluminum housing which supports two permanent bar magnets oriented such that the positive pole of one magnet is oriented to one end of the device and the positive pole of the other magnet is oriented to the other end of the device. The magnets are so housed in the aluminum die-cast housing so that they lie parallel and directly opposing one another across the non-ferrous pipe.

20 Claims, 5 Drawing Sheets

MAGNETIC WATER TREATMENT DEVICE

This is a continuation-in-part of co-pending application Ser. No. 06/934,568 filed on Nov. 21, 1986, now abandoned.

BACKGROUND OF THE INVENTION

1. Field

The invention is in the field of the magnetic treatment of water accomplished by orienting permanent magnets which are encased in an aluminum housing around a non-ferrous pipe. The invention further contemplates orienting other magnets, such as face charged ceramic magnets or electromagnets, around a pipe.

2. State of the Art

Improvement of water treatment technology has become one of the leading priorities in our present society. Inadequate water treatment technology has become a major problem in industry, power production, and home water supplies. It is desirable that water treatment systems do not require the use of reagents as part of the treatment process. In the search for such new water treatment methods it was discovered that a magnetic field from $10^2$ to $10^3$ oersteds is effective in preventing the formation of scales or encrustations in boilers and heating systems. After magnetic treatment, natural water does not, when heated, produce hard scales on the walls of boilers or heating pipes, but rather a loose sludge that settles to the bottom and can be easily removed or flushed without acid treatment.

A large number of papers pertinent to the magnetic treatment of water and how magnetic fields act on water, for what purposes magnetic treatment is effective, and under what conditions magnetic treatment is most effective and efficient, have been published in the Soviet Union during recent decades. Although a large amount of work has been done in this field, the mechanism by which a magnetic field affects the properties of water systems is still unknown. (Because this mechanism is not known, the problem of magnetic treatment of water is approached more on the engineering, empirical and technological level, rather than on a purely scientific basis.)

There continues to be some dispute on whether magnetic treatment is effective or not, however in the Soviet Union the magnetic treatment of water is used extensively with great economic effect. Our current body of knowledge does not resolve how to explain the observed phenomenon correctly. It is not understood whether the treatment phenomenon is due to changes which takes place within the water itself or is due solely to influence on the impurities present in the water. The conclusions drawn by the various authors based on laboratory experimentation are inconclusive. It is generally agreed that a magnetic field reduces the kinetics of crystallization processes and the freedom of movement of charged particles. The limitations of motion of particles in a field results in increases in the number of collisions and in the formation of crystallization centers. Magnetic treatment is effective if the liquid is passed between the poles of a magnet which has a sufficiently strong field and magnetic gradient, providing the temperature of the liquid is not too high. Magnetic treatment of water is widely used in boilers for all purposes and to increase the life of pipes in the oil, coal, and mining industries since it reduces corrosion and deposits of organic and inorganic compounds in the pipes.

The "magnetizations" process has come into widespread use and patents have been issued in most industrially developed countries of the world for various kinds of equipment for magnetic treatment of water. The manufacture of such equipment on a commercial scale has already begun and is currently in operation in the Soviet Union.

There has been a need for such devices suitable to home and small business use manufactured on an economically feasible basis and made available to the public.

SUMMARY OF THE INVENTION

According to the invention, a magnetic water treatment device structured to be placed in an approximating position to the outside diameter of home, small industrial and commercial water lines, to expose the flowing water to a magnetic flux field includes means providing a die-cast modality which provides means for securing permanent magnet rods held in approximating positions on either side of a non-ferrous pipe and held in place by means such as die-cast holes approximating one another in the die-cast halves of the means supporting the permanent magnets and held in place by non-ferrous bolts, such that the long axis of the magnet is parallel to the water flow.

The permanent magnets are oriented such that the positive pole of one magnet is oriented to one end of the device and the positive pole of the other magnet is oriented to the other end of the device. The magnets are so housed in the aluminum die-cast housing so that they lie in parallel and directly opposing one another across the non-ferrous pipe.

Preferably, the treatment device is for use with various sized non-ferrous water lines. The means supporting the permanent magnets is die-cast at diameters compatible with the outside diameter of the desired water pipe.

The described device provides means for four (4) magnetic flux fields which influence the magnetic character of the water flow through the pipe.

The accompanying drawings, which are incorporated in and constitute a part of this specification, illustrate the preferred embodiments of the invention and, together with the description, serve to explain the principles of the invention.

THE DRAWINGS

The accompanying drawings, which illustrate the best modes presently contemplated for carrying out the invention:

DETAILED DESCRIPTION OF THE ILLUSTRATED EMBODIMENTS

Figure 1:
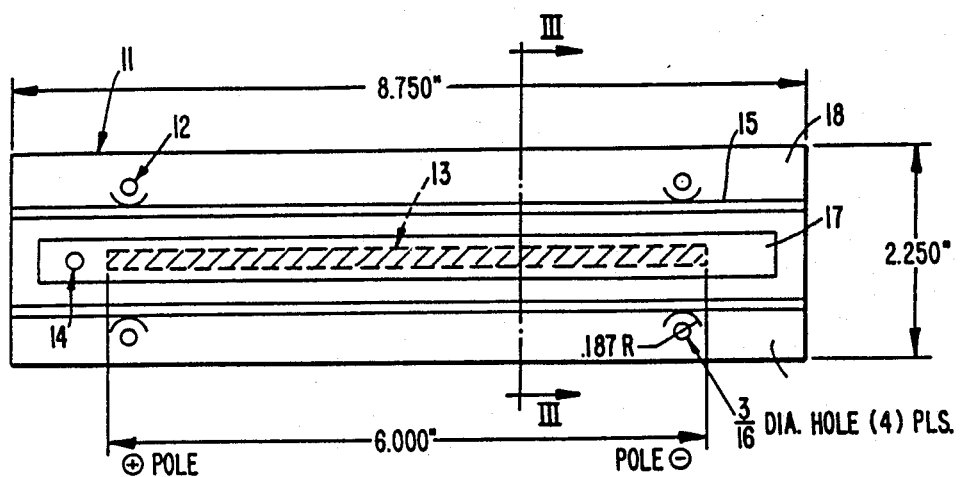
FIG. 1 is a top view of one of the halves of the aluminum housing which holds one of the magnetic bars.

Reference will now be made in detail to embodiments of the invention which are illustrated in the accompanying drawings. Throughout the drawings, like reference characters are used to designate like elements.

FIG. 1 depicts the top side of one half of the treatment device of the present invention. The treatment device includes a housing 11 which is made of die-cast aluminum. Four congruent holes 12 are provided in housing member 11 by which the two halves of the device are bolted together. The device is bolted on opposite sides of a non-ferrous pipe line. A cavity 17 is provided in housing member 11 in which a permanent magnet 13 is snapped into place. Magnet 13 is then covered with an epoxy resin. Also depicted in FIG. 1 is a polarity indicator 14 which is a die-cast hole in the aluminum housing in which a large colored glass bead is glued.

Figure 2:
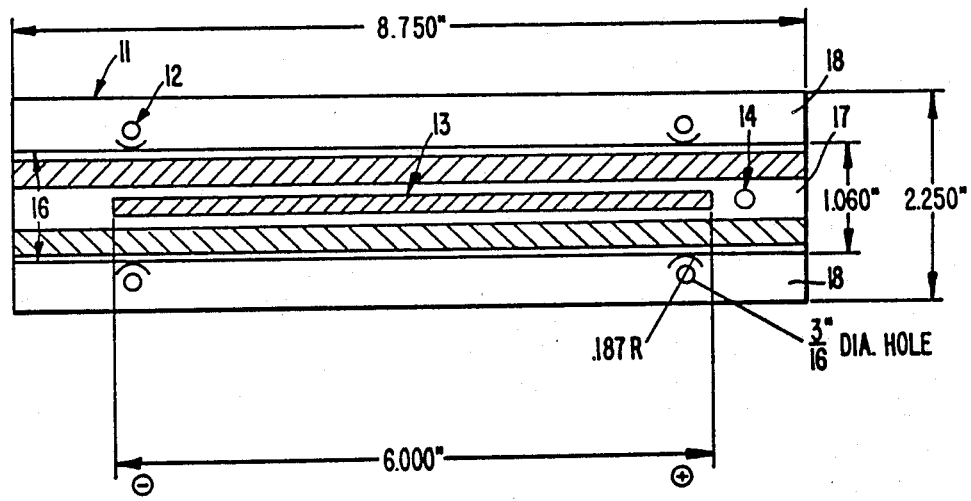
FIG. 2 is a bottom view of one of the die-cast aluminum housings which supports one of the magnetic bars.
Figure 3:
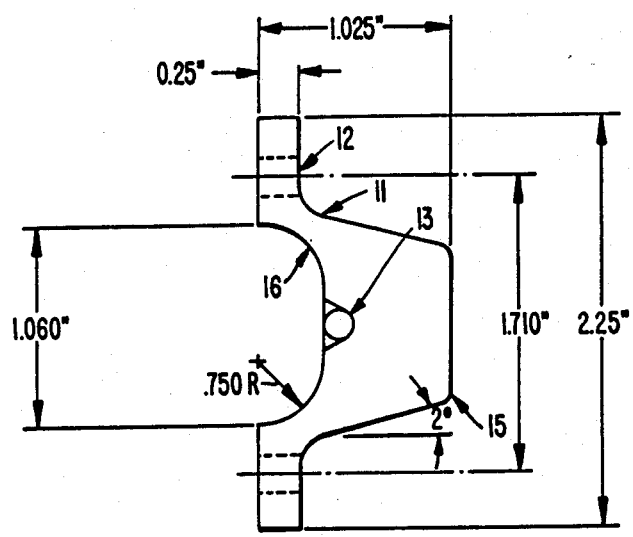
FIG. 3 is a cross-sectional view of one-half of the aluminum housing and magnetic bar taken along the line III—III of FIG. 1.

FIG. 2 depicts the underside of one-half of aluminum housing member 11. Congruent die-cast holes 12 are shown in elongated flanges 18 of housing member 11. Permanent magnet bar 13 is snapped into place in cavity 17. The bottom side of polarity indicator 14 is also visible in cavity 17. Polarity indicator 14 may comprise a colored glass bead on one end of housing member 11 for indicating proper orientation of the housing members. A semicircular indented portion 16 (as best shown in FIG. 3), makes up one-half of a "saddle" as shown in FIG. 2. Indented portion 16 is strapped to the pipe by bolting the two halves of the treatment device together.

FIG. 3 depicts a cross-sectional view of aluminum housing member 11 with die-cast congruent holes 12 for bolting the housing members together, permanent magnetic bar snapped in place and semicircular indented portion 16 which is designed to fit around one half of a non-ferrous pipe.

Figure 4:
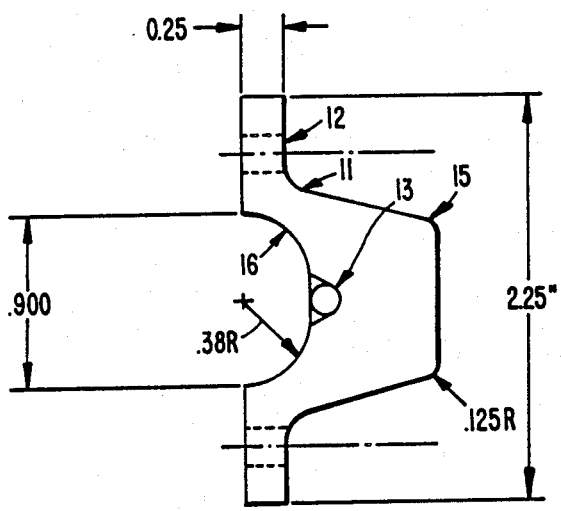
FIG. 4 is a cross-sectional view of the other half of the aluminum housing and magnetic bar.

FIG. 4 depicts the opposite half of the treatment device of the present invention. Another housing member 11 is shown which is identical to the housing member shown in FIG. 3, except for a smaller radius on the indented portion 16 which assists in making the treatment device compatible with a range of non-ferrous pipe sizes.

The opposite permanent bar magnets 13 are oriented such that the positive pole of one magnet is oriented to one end of the device and the positive pole of the other magnet is oriented to the other end of the device. The magnets are so housed in the aluminum die-cast housing that they lie in parallel and directly opposing one another across the non-ferrous water line.

Figure 5:
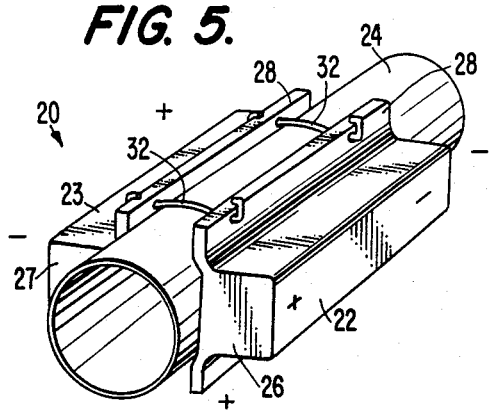
FIG. 5 is a prospective view of a water treatment device of another embodiment of the invention mounted on a pipe.
Figure 6:
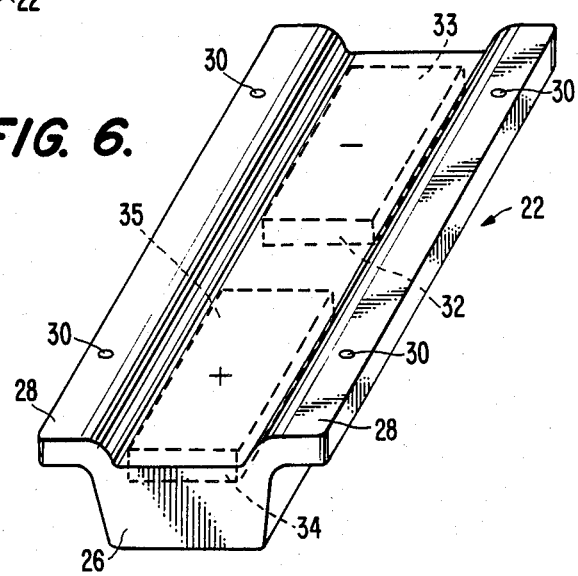
FIG. 6 is a perspective view of one of the individual treatment units of the device shown in FIG. 5.

FIGS. 5 and 6 depict another preferred embodiment of the invention. As shown in FIGS. 5 and 6, each magnetic treatment device 20 includes a treatment unit 22, a treatment unit 23, and a means for securing treatment units 22 and 23 to opposite sides of a pipe 24. Pipe 24 may be any metal, concrete, PCV or other type pipe. Each of the treatment units 22 and 23, as shown in FIG. 5, includes a housing 26 and 27, respectively, comprised of a non-ferrous material such as plastic, wood, brass, copper or aluminum. Preferably, housings 26 and 27 are comprised of a hard and rigid plastic that is resistant to melting or decomposition at high temperatures. Polystyrene and polypropylene plastics have been advantageously used to form housings 26 and 27 of the invention.

Treatment device 20 is provided with a means for securing treatment units 22 and 23 to opposite sides of pipe 24. As shown in FIGS. 5 and 6, housings 26 and 27 of treatment units 22 and 23 include elongated flanges 28 with a plurality of bores 30 through which fasteners 32 extend to secure treatment units 22 and 23 to each other on opposite sides of pipe 24. It is anticipated that treatment units 22 and 23 could be secured in numerous other ways, as for example, by adhesive, by welding, or by placing treatment units 22 and 23 in compartments built into opposite sides of pipe 24. It is further anticipated that housings 26 and 27 of treatment units 22 and 23 could be fully incorporated into the sides of pipe 24 itself.

Treatment unit 22 includes two magnetic bodies 32 and 34. Magnetic body 32 includes a negatively charged face 33 oriented in the same direction as a positively charged face 35 on magnetic body 34 when the magnetic bodies 32 and 34 are fixed in housing 26. Magnetic bodies 32 and 34 are preferably encased in housing 26, as shown in FIG. 6, but may be otherwise fixed in housing 26 by a variety of means such as forming housing 26 with a cavity or plurality of cavities into which magnetic bodies 32 and 34 are placed and sealed. Treatment units 22 and 23 are constructed identically.

Figure 7:
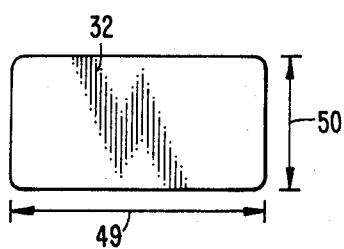
FIG. 7 is a plan view of the one of the magnets in the treatment unit shown in FIG. 6.

Magnetic bodies 32 and 34 are preferably each individual magnets having opposite faces on which oppositely charged magnetic poles reside. Face charged magnets are beneficially applied in the invention because they generate a magnetic flux over an entire face which can be oriented toward fluid flowing through a pipe. As shown in FIGS. 5, 6, and 7, magnets 32 and 34 may be of a rectangular shape with magnet 32 having a negatively charged face 33 and magnet 34 having a positively charged face 35, with each charged face 33 and 35 being oriented toward a pipe to which one of the treatment units is attached. Magnets 32 and 34 exert a magnetic flux great enough to penetrate a pipe to which treatment unit 22 or 23 is attached and are preferably high magnetic flux magnets such as face charged ceramic magnets. One such magnet is the Indox 5 TM ceramic magnet with an energy product of $3.5 \times 10^6$ Bd Hd manufactured by the Permag Division of the Dexter Corporation in Sunnyvale, Calif.

Each treatment unit 22 and 23 includes a means for indicating the polarity of the magnet faces oriented toward a pipe to which the magnetic treatment units 22 and 23 are attached. A positive "+" sign on the end of the treatment unit 22, holding magnet 34 with a positively charged face oriented toward pipe 24 to which the treatment unit 22 is to be attached, will serve this function. The opposite end of treatment unit 22, holding magnet 32 having a negatively charged face 33 oriented toward pipe 24 to which the treatment unit is to be attached, could be marked with a negative "−" sign. Treatment units 22 could be marked in other ways, as for example, coloring the positive and negative ends different colors or by marking just one end of the treatment unit with a sign to indicate the polarity of the treatment unit face oriented toward a pipe at the marked treatment unit end.

The two treatment units 22 and 23 of each magnetic treatment device 20 are marked so that they may be properly aligned on opposite sides of piper 24 as shown in FIG. 5. As shown in FIG. 5, treatment units 22 and 23 are oriented such that the positively charged face 35 of magnet 34 in treatment unit 22 is oriented opposite the negatively charged face of an identical magnet of treatment unit 23. Similarly, the negatively charged face 33 of magnet 32 in treatment unit 22 is oriented opposite a positively charged face of an identical magnet in treatment unit 23. The magnets are housed in housing members 26 and 27 such that they lie parallel and directly opposing one another across the pipe 24.

Figure 8:
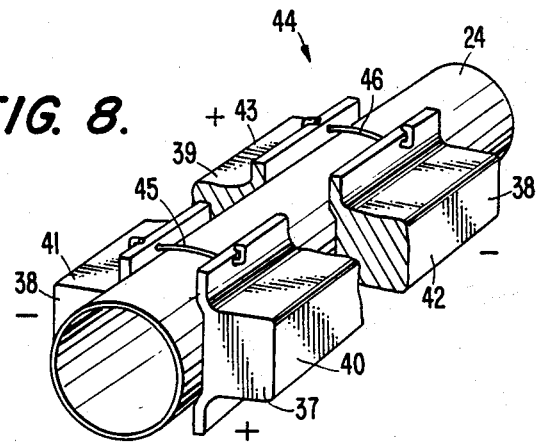
FIG. 8 is a perspective view of another embodiment of the invention.

It is anticipated that each treatment unit 22 could be otherwise embodied as two separate units 40 and 42 as shown in FIG. 8. As shown in FIG. 8, a magnetic treatment device 44 may include treatment unit 40 having a housing 36 encasing a magnet with a positively charged face oriented toward pipe 24 and fixed opposite treatment unit 41 having a housing 37 encasing a magnet with a negatively charged face oriented toward pipe 24, and treatment unit 42 having a housing 38 encasing a magnet with a negatively charged face oriented toward pipe 24 and fixed opposite treatment unit 43 having a housing 30 encasing a magnet with a positively charged face oriented toward pipe 24 directly opposite treatment unit 42. Treatment units 40-43 preferably hold a ceramic face charged magnet as discussed above with regard to FIGS. 5 and 6. Treatment units 40 and 41 are preferably attached to each other and secured to pipe 24 by fasteners 45 while treatment units 42 and 43 are similarly secured to fasteners 46.

When treatment units 40-43 are fixed to pipe 24, the distance between the magnets in treatment units 40 and 42 and the magnets in treatment units 41 and 43 is preferably less than the length of the magnets used in each treatment unit 40-43. In the preferred embodiments of the invention, the length 49 of magnets 32 or 34, as shown in FIG. 7 is approximately twice the width 50 of the magnet. In the embodiment of the invention shown in FIGS. 5 and 6, the distance between the two magnets in each treatment unit 22 and 23 is preferably less than the length 49 of the individual magnets. Preferably, magnets with a two inch length 49 are secured in housings 26 and 27 of FIG. 5 such that their ends are spaced 1¼ inches from each other. Similarly, in the embodiment of the invention shown in FIG. 8, the magnets in treatment units 40 and 42 and in opposing treatment units 41 and 43 are attached to pipe 24 in the same preferred spacial arrangement as the magnets in treatment units 22 and 23 of FIGS. 5 and 6.

Figure 9:
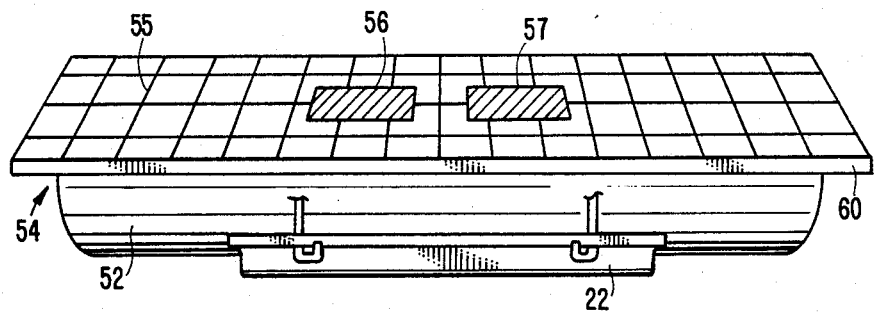
FIG. 9 is a forward perspective view of the treatment unit of FIG. 6 attached to half of a pipe for magnetic flux measurements.

FIG. 9 shows a single treatment unit 22 connected to the outside of a half section of PVC pipe 52 for the purpose of recording magnetic flux readings along the center half plane 54 of pipe 52. Magnetic flux readings in Gauss were measured for each square of grid 55 on center plane 54 shown in FIG. 9. The magnetic flux readings are recorded below in Table I. The treatment unit from which the data in Table I was measured included two face charged ceramic magnets approximately 2 inches in length and 1 inch in width which are represented by the rectangles 56 and 57 on grid 55. Each square in grid 55 corresponds to one square inch.

TABLE I

| −0 | +1 | −1 | −2 | −6  | −11 | −18 | −9  | +10 | +21 | +17 | +5 | +1 | +0 | +0 | +0 |
| −0 | −0 | −1 | −2 | −9  | −26 | −39 | −20 | +18 | +49 | +30 | +8 | +0 | −0 | −0 | +1 |
| −0 | −0 | −0 | −2 | −8  | −28 | −41 | −22 | +18 | +40 | +28 | +7 | +0 | −0 | −1 | −1 |
| −0 | −0 | −0 | −1 | −4  | −13 | −18 | −12 | +8  | +20 | +12 | +4 | −0 | −0 | −0 | −1 |

Figure 11:
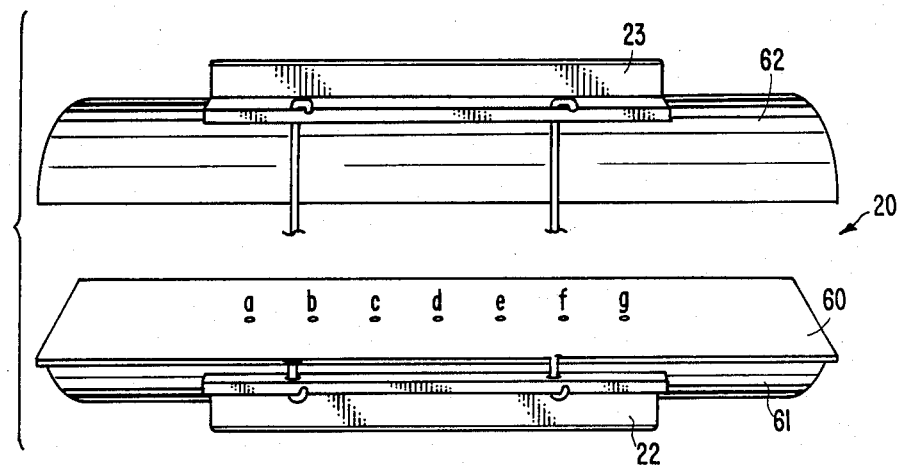
FIG. 11 is a forward perspective view like FIG. 10 showing another magnetic flux measurement condition.
Figure 10:
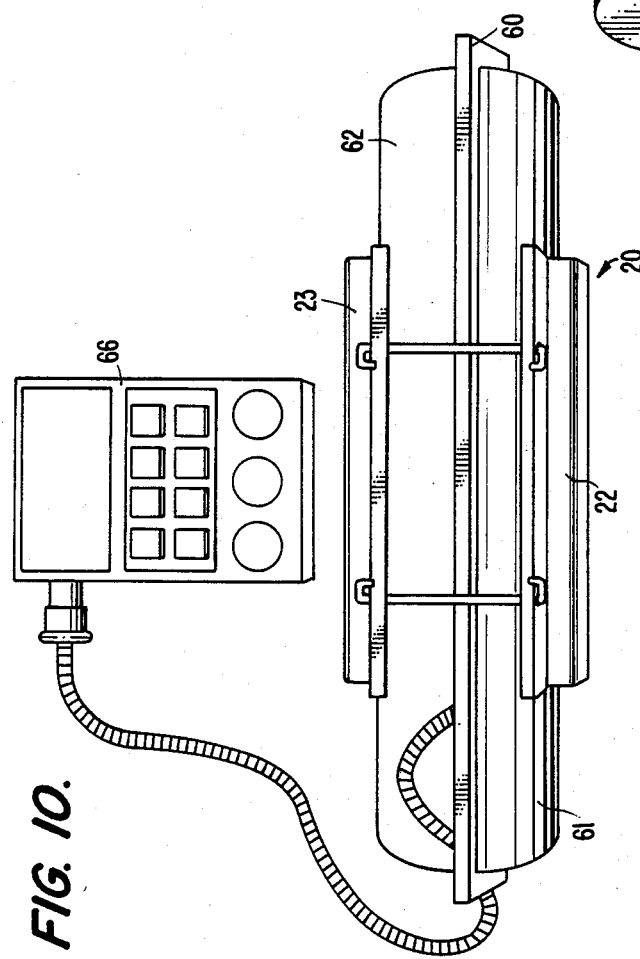
FIG. 10 is a forward perspective view of a magnetic treatment device of FIG. 5 on a split pipe for magnetic flux measurements.

FIGS. 10 and 11 show a second magnetic flux test conducted on magnetic treatment device 20. As shown in FIG. 10, a section of PVC pipe was cut into halves 61 and 62. Treatment units 22 and 23 were attached to the outside of each pipe half 61 and 62, respectively. As shown in FIG. 11, seven measurement points, labeled a-g, at ½ inch intervals were plotted on a piece of plexiglass 60 placed on the central plane dividing pipe half 61 from pipe half 62. A magnetic flux measurement was taken with a Gauss meter 66 at each point under three different conditions. First, the magnetic flux was measured at each point (a-g) with the pipe halves closed and the treatment units 22 and 23 oriented according to the present invention as shown in FIG. 10. That is, the positive charged magnetic face of the magnet of treatment device 22 was oriented directly opposite the negative charged magnetic face of treatment device 23 and the negative charged magnetic face of treatment device 22 was oriented directly opposite the positive charged magnetic face of treatment device 23. In Table II below, this orientation is referred to as "attracting mode".

Second, the orientation of the second treatment unit 23 was reversed such that the negative charged magnetic face of unit 22 faced a negative charged magnetic face of unit 23 and the positive charged magnetic face of unit 22 faced the positive charged magnetic face of unit 23. In Table II below, this is referred to as "repelling mode".

Third, pipe half 62 and treatment unit 23 were removed and magnetic flux measurements were recorded for the seven points shown in FIG. 11 with the magnetic action of a single treatment unit. In Table II below, these measurements are referred to as "single mode".

TABLE II

|                 | a   | b   | C   | d  | e   | f   | g   |
|-----------------|-----|-----|-----|----|-----|-----|-----|
| Attracting mode | −19 | −47 | −49 | −8 | +46 | +60 | +26 |
| Repelling mode  | −12 | −38 | −33 | 0  | +36 | +44 | +10 |
| Single mode     | −16 | −40 | −38 | −2 | +39 | +48 | +18 |

Table II clearly shows that magnetic flux along the center line of the pipe was greatest when the treatment units 22 and 23 were placed in the attracting mode used in magnetic treatment device 20 of the present invention. For each point, the magnetic flux in the attracting mode was greater than when treatment units 22 and 23 were arranged in the repelling mode or when treatment unit 22 was used in the single mode. This greater degree of magnetic flux helps explain many of the beneficial results obtained with the magnet treatment device 20 of this invention.

Figure 12:
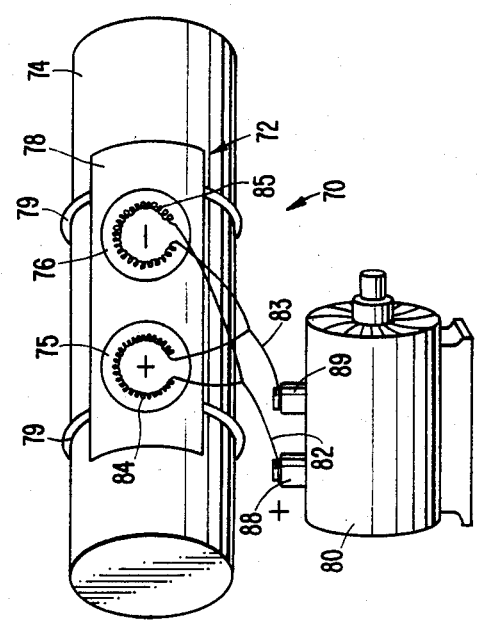
FIG. 12 is a perspective view of an alternative embodiment of the invention.

According to another embodiment of the invention an electromagnetic treatment device 70 can be applied to a pipe 74 as shown in FIG. 12. Treatment device 70 includes a treatment unit 72 arranged opposite another treatment unit (not shown) identical to treatment unit 72. Treatment unit 72 includes electromagnetic heads 75 and 76 embedded in or bonded to a rigid housing 78 comprised of non-ferrous material such as fiberglass. Housing 78 of treatment unit 72 is secured to pipe 74 and to the opposing treatment unit by fasteners 79 comprising high-strength wires or bands. It is anticipated that the treatment units could be secured to pipe 74 by other means including adhesives, welding, or specially built chambers in the sides of pipe 74 for receiving opposing treatment units. It is further anticipated that housing 78 and the opposing treatment unit housing could be fully incorporated into the sides of pipe 74.

Electromagnetic heads 75 and 76. Each include copper coils 84, 85, respectively wound around a ring-shaped cast iron core. For example, a suitale electromagnet can be made using a 5" outer diameter and $4\frac{1}{2}$" inner diameter, cast iron core wound with 3200 turns of #22 copper wire. As shown in FIG. 12, coil 84 in electromagnetic head 75 and coil 85 in electromagnetic head 76 are each connected to a DC generator 80 by wires 82 and 83. Coils 84 and 85 are connected to poles 88 and 89 of generator 80, such that electromagnetic heads 75 and 76 generate opposite magnetic flux fields. The treatment unit on the opposite side of pipe 74 is identical to treatment unit 72 except that the electromagnetic heads are connected to DC generator 80 in an opposite manner such that the electromagnetic head directly opposite positive head 75 generates a negative magnetic field while the electromagnetic head directly opposite negative electromagnetic head 76 generates a positive magnetic field.

In operation, the treatment device is attached to a pipe thereby exposing the pipe to a magnetic flux field of sufficient strength to alter the ionic and/or magnetic characteristics of the fluid in the pipe. This alteration changes the behavior and character of the fluid and causes it to purge the pipe of deposits and scale and prevent the reformation of such deposits and scale. In many instances, the treatment device of the present invention improves the taste of water and alters water's ability to stabilize emulsions such as soap, such that consumers using water treated by the present invention use less soap and soap products.

As shown in Tables I and II the magnetic treatment device of FIGS. 5 and 6 efficiently generates a magnetic flux field across the interior of a moderately sized pipe. For larger pipes, it is expected that the electromagnetic treatment device 70, shown in FIG. 12, could be used to treat fluid in pipes of 16 to 18 inches in diameter if electromagnetic heads 75 and 76 were 5" diameter heads capable of handling 6 amps and 60 volts of DC current. Of course, it is anticipated that larger magnetic fluxes could be obtained and that the electromagnetic treatment devices could be used on larger diameter pipes if larger electromagnetic heads or a more powerful DC currents were used.

In addition to the benefits already listed, the magnetic treatment device of the present invention can be beneficially applied in the treatment of water having high iron, sulfur, chlorine, organic tannin or acid contents so as to improve the taste and other properties of water or other liquid treated. It has also been found that the treatment device of the present invention helps reduce mineral and organic deposits on the inside of pipes and can even be applied to help open pipes that have been previously restricted by scale deposits. Fluid passed through the magnetic treatment device of the invention has been found to have an altered, more homogeneous, nature than untreated water. The treated water has a reduced surface tension and improved wetting agent characteristics. These improved properties have been found to be advantageous in numerous applications including swimming pools, washing machines, coffee brewers, livestock water supplies and ice rink glazing.

It will be apparent to those skilled in the art that modifications and variations can be made in the treatment device of this invention. The invention in its broader aspects is, therefore, not limited to the specific details, representative apparatus, and illustrative examples shown and described above. Thus, it is intended that all matter contained in the foregoing description or shown in the accompanying drawings shall be interpreted as illustrative and not in a limiting sense.

I claim:

1. A treatment device for magnetically treating fluid flowing through a pipe, comprising:

a first elongated housing member having two opposite ends in an elongated abutment side for abutting said pipe;

first permanent magnet means fixed in said first housing member, said first permanent magnet means having a positive pole facing the housing member pipe abutment side oriented to one end of said first housing member, and a negative pole facing the housing member pipe abutment side oriented to the opposite end of said first housing member;

a second elongated housing member having two opposite ends and an elongated abutment side for facing said pipe;

second permanent magnet means fixed in said second housing member, said second permanent magnet means having a positive pole facing the housing member pipe abutment side oriented to one end of said second housing member, and a negative pole facing the housing member pipe abutment side oriented to the opposite end of said second housing member; and attachment means for fixing said abutment sides of said first and second housing members against the pipe, said attachment means holding said first and second housing members on opposing sides of the pipe, said positive magnetic pole facing the pipe and oriented to one end of said first housing member opposing said negative magnetic pole facing the pipe and oriented to one end of said second housing member, and said negative magnetic pole facing the pipe and oriented to the opposite end of said first housing member opposing said positive magnetic pole facing the pipe and oriented to the opposite end of said second housing member.

2. The treatment device of claim 1 wherein
said first elongated housing member has a cavity in said abutment side thereof and said first permanent magnet means is fixed in said cavity of said first housing member,
said second elongated housing member has a cavity in said abutment side thereof and said second permanent magnet means is fixed in said cavity of said second housing member, and
said attachment means hold said respective abutment sides of said first and second housing members against opposing sides of the pipe.

3. The treatment device of claim 2 wherein said first and second permanent magnet means comprise first and second elongated permanent bar magnets, respectively, said first and second bar magnets each having a positive pole at one end and a negative pole at an opposite end.

4. The treatment device of claim 3 wherein said first and second bar magnets are each single magnets having a positive pole at one end and a negative pole at the other end.

5. The treatment device of claim 3 wherein said cavities in said first and second elongated housing members are each elongated cavities extending substantially the entire length of said first and second elongated housing members.

6. The treatment device of claim 5 wherein said first and second elongated housing members each have an elongated indented portion having a substantially semi-circular cross section on the respective abutment sides thereof, the radius of said indented portions of said first and second housing members substantially corresponding to the pipe outer radius, the cavities of said first and second housing members each opening into said elongated indented portions of said first and second housing members, respectively.

7. The treatment device of claim 6 wherein said attachment means comprises two elongated flanges extending along opposite sides of each of said indented portions of said first and second housing members, and a plurality of fasteners extending between said flanges of said first and second housing members.

8. The treatment device of claim 6 wherein said first and second housing members are comprised of aluminum.

9. The treatment device of claim 3 wherein said first and second housing members each include polarity indication means for indicating the end of each housing member containing said positive magnetic pole and the end of each housing member containing said negative magnetic pole.

10. A treatment device for magnetically treating fluid flowing through a non-ferrous pipe, comprising:
a first elongated aluminum housing member having an elongated cavity on a first side thereof, said first housing member having two opposite ends;
a first elongated permanent bar magnet fixed in said elongated cavity of said first housing member, said first bar magnet having a side with a positive pole thereon facing out of said cavity and oriented to one end of said first housing member, and having a side with a negative pole thereon facing out of said cavity and oriented to the opposite end of said first housing member;
a second elongated aluminum housing member having an elongated cavity on a first side thereof, said second housing member having two opposite ends;
a second elongated permanent bar magnet fixed in said elongated cavity of said second housing member, said second bar magnet having a side with a positive pole thereon facing out of said cavity and oriented to one end of said second housing member, and having a side with a negative pole thereon facing out of said cavity oriented to the opposite end of said second housing member;
attachment means for fixing said respective first sides of said first and second housing members against the non-ferrous pipe, said attachment means holding said first and second housing members on opposing sides of the pipe, said positive magnetic pole oriented to one end of said first housing member opposing said negative pole oriented to one end of said second housing member, and said negative magnetic pole oriented to the opposite end of said first housing member opposing said positive magnetic pole oriented to the opposite end of said second housing member.

11. A treatment device for magnetically treating fluid flowing through a pipe, comprising:
a first treatment unit having two opposite ends, said first treatment unit including,
a first housing member having an abutment side for abutting the pipe,
first magnet means fixed in said first housing member, said first magnet means having a positive pole facing the first housing member pipe abutment side;
a second housing member having an abutment side for abutting the pipe,
second magnet means fixed in said second housing member, said second magnet means having a negative pole facing the second housing member abutment side;
a second treatment unit having two opposite ends, said second treatment unit including,
a third housing member having an abutment side for abutting the pipe,
third magnet means fixed in said third housing member, said third magnet means having a negative pole facing the third housing member abutment side;
a fourth housing member having an abutment side for abutting the pipe,
fourth magnetic means fixed in said fourth housing member, said fourth magnet means having a positive pole facing the fourth housing member abutment side;
attachment means for fixing said abutment sides of said first and second housing members of said first treatment unit and said abutment sides of said third and fourth housing members of said second treatment unit against the pipe, said attachment means holding said first and second housing members on one side of the pipe and holding said third and fourth housing members on an opposite side of the pipe, said positive magnetic pole of said first housing member being oriented opposite said negative magnetic pole of said third housing member, and said negative magnetic pole of said second housing member being oriented opposite said positive magnetic pole of said fourth housing member.

12. The treatment device of claim 11 wherein said first and second housing members of said first treatment unit are interconnected, and said third and fourth housing members of said second treatment unit are interconnected.

13. The treatment device of claim 11 wherein
said first and second magnet means of said first treatment unit have lengths in the longitudinal direction of the pipe, that are substantially equal, and said first and second magnet means are spaced from each other by an amount less than the length of said first and second magnet means; and
said third and fourth magnet means of said second treatment unit have lengths in the longitudinal direction of the pipe, that are substantially equal, and said third and fourth magnet means are spaced from each other by an amount less than the length of said third and fourth magnet means.

14. The treatment device of claim 11 wherein said first, second, third and fourth housing members are comprised of plastic.

15. The treatment device of claim 11 wherein said first, second, third, and fourth magnet members each have two opposite faces, one being a positively charged magnetic pole and the other being a negatively charged magnetic pole, and wherein one of said charged faces is oriented toward the pipe when the treatment device is fixed on the pipe.

16. The treatment device of claim 15 wherein said first, second, third and fourth magnet members are ceramic magnetic.

17. A treatment device for magnetically treating fluid flowing through a pipe, comprising:
a first elongated housing member having two opposite ends and an elongated abutment side for abutting the pipe;
a first ceramic magnet fixed in said first housing member, said first ceramic magnet having a face with a positive magnetic pole thereon facing the housing member pipe abutment side proximate one end of said first housing member, and a second ceramic magnet fixed in said first housing member, said second ceramic magnet having a face with a negative magnetic pole thereon facing the housing member pipe abutment side proximate the opposite end of said first housing member;
a second elongated housing member having two opposite ends and an elongated abutment side for facing the pipe;
a third ceramic magnet fixed in said second housing member, said third ceramic magnet having face with a negative magnetic pole thereon facing the housing member pipe abutment side proximate one end of said second housing member, and
a fourth ceramic magnet fixed in said second housing member, said fourth ceramic magnet having a face with a positive magnetic pole thereon facing the housing member pipe abutment side proximate the opposite end of said second housing member;
attachment means for fixing said abutment sides of said first and second housing members against the pipe, said attachment means holding said first and second housing members on opposite sides of the pipe, said positive magnetic pole facing the pipe in said first housing member and being oriented opposite said negative magnetic pole facing the pipe in said second housing member, and said negative magnetic pole facing the pipe in said first housing member and being oriented opposite said positive magnetic pole facing the pipe in said second housing member.

18. The treatment device of claim 17 wherein said attachment means comprises two elongated flanges extending along opposite sides of each of said first and second housing members and a plurality of fasteners extending between said flanges of said first and second housing members.

19. A treatment device for electromagnetically treating fluid flowing through a pipe, comprising:
a first elongated housing member having two opposite ends and an elongated abutment side for abutting said pipe;
a first electromagnet in said first housing member, said first electromagnet having a positive magnetic pole facing the housing member pipe abutment side proximate one end of said first housing member, and a second electromagnet fixed in said first housing member, said second electromagnet having a negative pole facing the housing member pipe abutment side proximate the opposite end of said first housing member, said first and second electromagnets being electrically connected to a direct current generator;
a second elongated housing member having two opposite ends and an elongated abutment side for facing said pipe;
a third electromagnet fixed in said second housing member, said third electromagnet having a negative pole facing the housing member pipe abutment side proximate one end of said second housing member and a fourth electromagnet fixed in said second housing member, said fourth electromagnet having a positive pole facing the housing member pipe abutment side proximate the opposite end of said second housing member, said third and fourth electromagnets being electrically connected to a direct current generator;
attachment means for fixing said abutment sides of said first and second housing members against the pipe, said attachment means holding said first and second housing members on opposite sides of the pipe, said positive magnetic pole facing the pipe in said first housing member and being oriented opposite said negative magnetic pole facing pipe in said second housing member, and said negative magnetic pole facing the pipe in said first housing member and being oriented opposite said positive magnetic pole facing the pipe in said second housing member.

20. The treatment device of claim 19 wherein said first, second, third and fourth electromagnets each comprise a ring-shaped cast iron core wound with copper wire.

* * * * *

UNITED STATES PATENT AND TRADEMARK OFFICE
CERTIFICATE OF CORRECTION

PATENT NO. : 4,888,113
DATED : December 19, 1989
INVENTOR(S) : Robert R. Holcomb It is certified that error appears in the above—identified patent and that said Letters Patent is hereby corrected as shown below:

Column 8, line 36, "in" should read -- and --.

Column 10, line 48, "magnetic" should read -- magnet --.

Signed and Sealed this

Sixteenth Day of July, 1991

*Attest:*

HARRY F. MANBECK, JR.

*Attesting Officer*  *Commissioner of Patents and Trademarks*